(12) United States Patent
Nomura et al.

(10) Patent No.: US 9,535,241 B2
(45) Date of Patent: Jan. 3, 2017

(54) STRUCTURED ILLUMINATING MICROSCOPY AND STRUCTURED ILLUMINATING OBSERVATION METHOD

(71) Applicant: NIKON CORPORATION, Tokyo (JP)

(72) Inventors: Tatsushi Nomura, Sagamihara (JP); Hisao Osawa, Kashiwa (JP); Naoki Fukutake, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 372 days.

(21) Appl. No.: 14/068,799

(22) Filed: Oct. 31, 2013

(65) Prior Publication Data

US 2014/0055594 A1 Feb. 27, 2014

Related U.S. Application Data

(63) Continuation of application No. PCT/JP2012/002946, filed on May 1, 2012.

(30) Foreign Application Priority Data

May 6, 2011 (JP) ................................ 2011-103652

(51) Int. Cl.
G02B 21/06 (2006.01)
G02B 21/14 (2006.01)
G01N 21/64 (2006.01)

(52) U.S. Cl.
CPC ............... *G02B 21/06* (2013.01); *G02B 21/14* (2013.01); *G01N 21/6456* (2013.01)

(58) Field of Classification Search
CPC ...... G01N 21/6456; G02B 21/06; G02B 21/14
(Continued)

(56) References Cited

U.S. PATENT DOCUMENTS 3,657,473 A * 4/1972 Corcoran ................. G03H 1/28
347/255
6,239,909 B1 5/2001 Hayashi et al.
(Continued)

FOREIGN PATENT DOCUMENTS

JP A-2007-199572 8/2007
JP A-2007-279287 10/2007
(Continued)

OTHER PUBLICATIONS

Mats G. L. Gustafsson et al., "Doubling the lateral resolution of wide-field fluorescence microscopy using structured illumination", Proceedings of the SPIE—The International Society for Optical Engineering, vol. 3919, pp. 141-150, 2000.*

(Continued)

*Primary Examiner* — Mohammed Rahaman
(74) *Attorney, Agent, or Firm* — Oliff PLC

(57) ABSTRACT

In order to realize a high-speed switching of structured pattern, a structured illuminating microscopy includes a driving unit generating a sonic standing wave in a sonic wave propagation path by giving a driving signal for vibrating a medium of the sonic wave propagation path to a light modulator, an illuminating optical system making at least three diffracted components of the exit light flux passed through the sonic wave propagation path to be interfered with one another, and forming interference fringes on an observational object, an image-forming optical system forming an image by an observational light flux from the observational object on a detector, and a controlling unit controlling a contrast of an image by modulating at least one of an intensity of the exit light flux, an intensity of the observational light flux, and the detector with a modulating signal of 1/N frequency of the driving signal.

13 Claims, 10 Drawing Sheets

(58) Field of Classification Search
USPC .......................................................... 348/79
See application file for complete search history.

(56) References Cited

U.S. PATENT DOCUMENTS

| RE38,307 E | 11/2003 | Gustafsson et al. |
| 8,115,806 B2 | 2/2012 | Osawa et al. |
| 2011/0182529 A1* | 7/2011 | Kempe .............. G01N 21/6458 382/274 |

FOREIGN PATENT DOCUMENTS

| WO | WO 2007/043313 A1 | 4/2007 |
| WO | WO 2009/043545 A1 | 4/2009 |
| WO | WO 2009/043546 A1 | 4/2009 |
| WO | WO 2010/037487 A1 | 4/2010 |

OTHER PUBLICATIONS

Lukosz, "Optical Systems with Resolving Powers Exceeding the Classical Limit. II," *Journal of the Optical Society of America*, Jul. 1967, pp. 932-941, vol. 57, No. 7.

Gustaffson et al., "Doubling the lateral resolution of wide-field fluorescence microscopy using structured illumination," *Three-Dimensional and Multidimensional Microscopy: Image Acquisition Processing VII*, 2000, pp. 141-150, vol. 3919.

International Search Report issued in International Patent Application No. PCT/JP2012/002946 dated Jul. 17, 2012.

Nov. 12, 2013 International Preliminary Report on Patentability issued in International Application No. PCT/JP2012/002946 (with translation).

* cited by examiner

FIG. 13
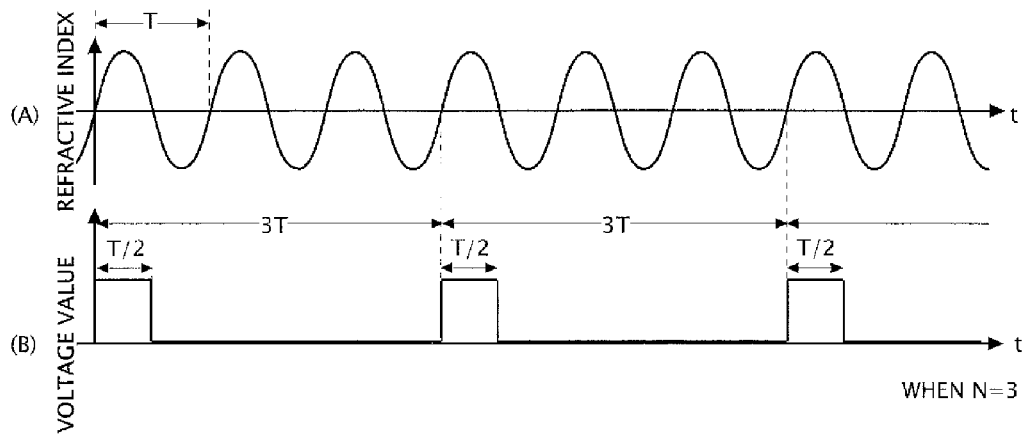
WHEN N=3
FIG. 14
| | a | b | c | d | e | f |
|---|---|---|---|---|---|---|
| AMOUNT OF CHANGE IN NUMBER OF WAVE (NUMBER) | 0 | 1/2 | 1 | 3/2 | 2 | 5/2 |
| AMOUNT OF PHASE SHIFT OF FRINGE (rad) | 0 | $2\pi/6$ | $2(2\pi)/6$ | $3(2\pi)/6$ | $4(2\pi)/6$ | $5(2\pi)/6$ |
D:L=1:6
FIG. 15
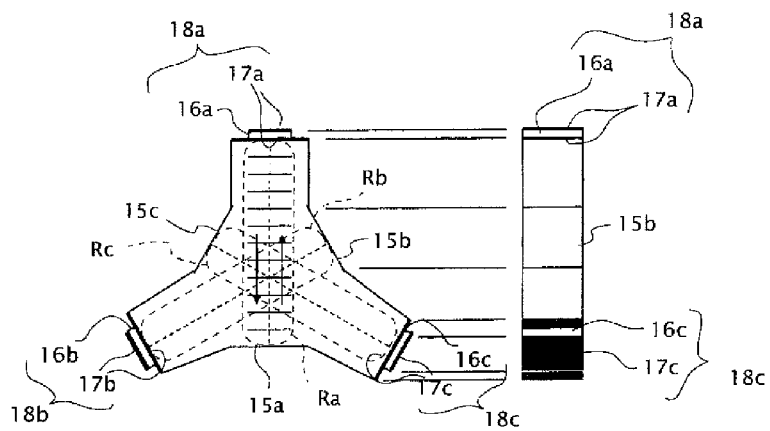

STRUCTURED ILLUMINATING MICROSCOPY AND STRUCTURED ILLUMINATING OBSERVATION METHOD

CROSS REFERENCE TO RELATED APPLICATION

This application is a continuation application of International Application No. PCT/JP2012/002946, filed on May 1, 2012, designating the U.S., and claims the benefit of priority from Japanese Patent Application No. 2011-103652, filed on May 6, 2011, the entire contents of which are incorporated herein by reference.

BACKGROUND

1. Field

The present application relates to a structured illuminating microscopy and a structured illuminating observation method.

2. Description of the Related Art

A super-resolution microscopy is one that modulates an illumination light flux that illuminates a sample plane and demodulates an image-forming light flux which is incident on a position that is substantially conjugated with the sample plane of an image-forming optical system, in order to make information regarding a high spatial frequency that exceeds a resolution limit (diffracted light at a large angle) out of diffracted light that exits from a sample, to be contributed to an image formation (refer to Non-Patent Document 1: W. Lukosz, "Optical systems with resolving powers exceeding the classical limit. II", Journal of the Optical Society of America, Vol. 57, PP. 932-941, 1967, Non-Patent Document 2: Mats G. L. Gustafsson et al., "Doubling the lateral resolution of wide-field fluorescence microscopy using structured illumination", Proceedings of the SPIE—The International Society for Optical Engineering, Vol. 3919, pp. 141-150, 2000, Patent Document 1: U.S. Pat. No. 6,239,909, Patent Document 2: Specification of U.S. Pat. No. RE 38307, Patent Document 3: U.S. Pat. No. 8,115,806, and the like).

In a method of Non-Patent Document 1, a diffraction grating (diffraction grating for modulation) is disposed in the vicinity of a sample plane, and a diffraction grating (diffraction grating for demodulation) having a grating constant which is conjugated with that of the diffraction grating for modulation, is disposed at a position which is substantially conjugated with the sample plane of an image-forming optical system. When those two diffraction gratings are moved in a conjugated manner, it becomes possible to observe a structure of sample by separating it from patterns of the diffraction gratings.

Meanwhile, Patent Document 1 discloses an example in which a structured illuminating microscopy is applied to a fluorescent observation. In a method of Patent Document 1, a light flux that exits from a coherent light source is split into two light fluxes by a diffraction grating, and those two light fluxes are individually condensed on mutually different positions on a pupil of an objective lens. At this time, the two light fluxes exit from the objective lens as collimated light fluxes with different angles, and overlap each other on a sample plane to form striped interference fringes. Accordingly, the sample plane is subjected to structured illumination. Further, in the method of Patent Document 1, images of sample images are repeatedly obtained while shifting a phase of the structured illumination in steps, and calculation corresponding to the aforementioned separation (separating calculation) and calculation corresponding to the aforementioned demodulation (demodulating calculation) are performed on the obtained plurality of images.

Note that as a method of shifting the phase of structured illumination in steps, there are a method in which a wedge-shaped prism is inserted into one of the above-described two light fluxes and moved in steps in a direction perpendicular to an optical axis, a method in which a diffraction grating is moved in steps in a direction perpendicular to a grid line, a method in which a sample is moved in steps in a pitch direction of structured illumination, and the like.

However, when an optical element is moved in steps, a certain period of time is required for stopping the moving optical element at an appropriate position, so that it is difficult, in the method of Patent Document 2, to reduce a period of time taken for obtaining all of the required images. Particularly, when a sample being an observational object is an organism specimen, there is a chance that a structure of the sample changes every second, so that the obtainment of images should be performed as fast as possible.

Further, as an application of technique utilizing the interference fringes (Patent Document 1), a technique of turning a beam that contributes to the interference fringe into three beams (Non-Patent Document 2) has also been proposed for achieving a super-resolution effect in both of an in-plane direction and a depth direction of a sample. This is because, if three beams are used, a stripe pattern of structured illumination can be generated not only in the in-plane direction but also in the depth direction. However, in that case, the number of images required for the aforementioned separating calculation is increased, so that it can be considered that the necessity of increasing the speed of obtaining images is particularly high.

SUMMARY

The present invention has been made to solve the problems of the related art described above. A proposition of the present invention is to provide a structured illuminating microscopy and a structured illuminating observation method capable of performing a high-speed switching of structured pattern, and expanding a structuring direction.

One aspect of a structured illuminating microscopy of the present invention includes a light modulator disposed in a light path of an exit light flux from a light source, and in which a sonic wave propagation path is arranged in a direction traversing the exit light flux, a driving unit generating a sonic standing wave in the sonic wave propagation path by giving a driving signal for vibrating a medium of the sonic wave propagation path to the light modulator, an illuminating optical system making at least three diffracted components of the exit light flux passed through the sonic wave propagation path to be interfered with one another, and forming interference fringes of the diffracted components on an observational object, an image-forming optical system forming an image by an observational light flux from the observational object on a detector, and a controlling unit controlling a contrast of an image obtained from the detector by modulating at least one of an intensity of the exit light flux, an intensity of the observational light flux, and the detector with a modulating signal having a frequency which is 1/N times a frequency of the driving signal (where N is an integer of 1 or more).

One aspect of a structured illuminating observation method of the present invention includes a light modulating step of preparing a light modulator disposed in a light path of an exit light flux from a light source, and in which a sonic wave propagation path is arranged in a direction traversing the exit light flux, a driving step of generating a sonic standing wave in the sonic wave propagation path by giving a driving signal for vibrating a medium of the sonic wave propagation path to the sonic wave spatial light modulator, an illuminating step of making at least three diffracted components of the exit light flux passed through the sonic wave propagation path to be interfered with one another, and forming interference fringes of the diffracted components on an observational object, an image-forming step of forming an image by an observational light flux from the observational object on a detector, and a controlling step of controlling a contrast of an image obtained from the detector by modulating at least one of an intensity of the exit light flux, an intensity of the observational light flux, and the detector with a modulating signal having a frequency which is 1/N times a frequency of the driving signal (where N is an integer of 1 or more).

BRIEF DESCRIPTION OF THE DRAWINGS

FIG. 12A illustrates a waveform when a phase difference M is a product of $\pi/2$ multiplied by an even number, FIG. 12B illustrates a waveform when the phase difference $\Delta\Psi$ is not a product of $\pi/2$ multiplied by an odd number, and FIG. 12C illustrates a waveform when the phase difference $\Delta\Psi$ is a product of $\pi/2$ multiplied by an odd number.

FIG. 13(A) illustrates a waveform of time-variation of a refractive index of antinode a of a standing wave in FIG. 7, and FIG. 13(B) illustrates a waveform of time-variation of an intensity of incident light (note that a case where N=3 is illustrated).

FIG. 14 is a diagram explaining a phase shift pitch under a setting of D:L=1:6.

FIG. 15 is a modified example of the ultrasonic wave spatial light modulator 3.

DETAILED DESCRIPTION OF THE EMBODIMENT

Hereinafter, a structured illuminating microscopy system will be described as an embodiment of the present invention.

Figure 1:
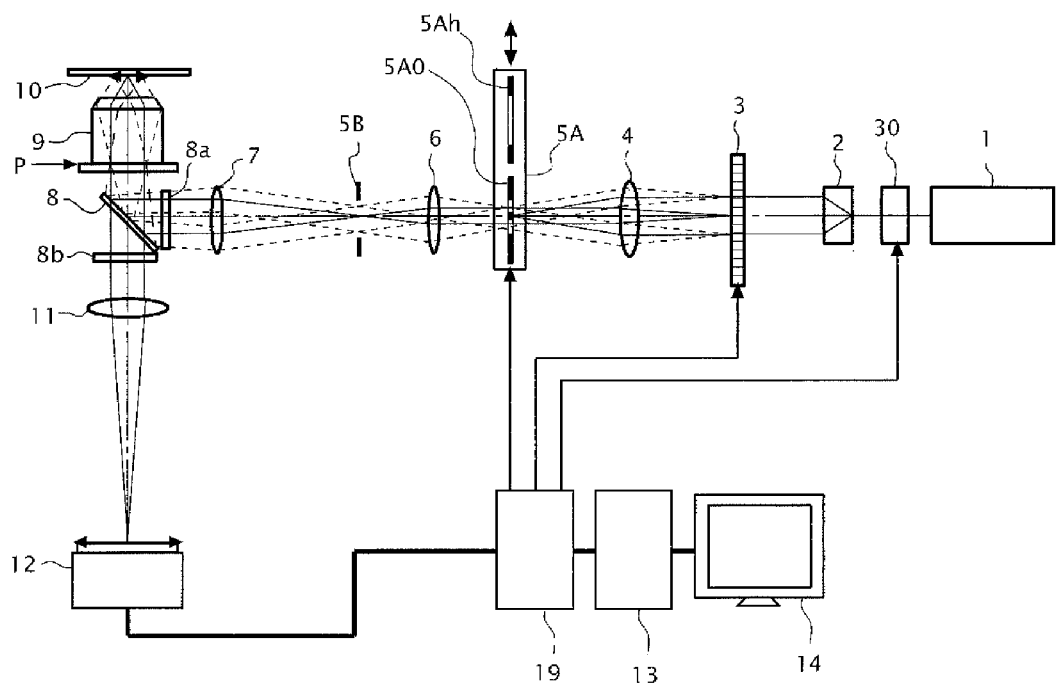
FIG. 1 is a configuration diagram of a structured illuminating microscopy system of an embodiment.

FIG. 1 is a configuration diagram of a structured illuminating microscopy system of the present embodiment. As illustrated in FIG. 1, in the present system, there are disposed a coherent light source 1, a light intensity modulator 30, a collector lens 2, an ultrasonic wave spatial light modulator 3, a lens 4, a mask switching mechanism 5A, a lens 6, a field stop 5B, a lens 7, an excitation filter 8a, a dichroic mirror 8, a fluorescence filter 8b, a second objective lens 11, an imaging device (CCD camera or the like) 12, a controlling device 19, an image storing-calculating device (computer or the like) 13, an image displaying device 14, and an objective lens 9. Note that a reference numeral 10 in FIG. 1 denotes a specimen placed on a not-illustrated stage, and in this case, it is assumed that the specimen is previously fluorescent-stained.

The coherence light source 1 radiates light having a wavelength which is the same as an excitation wavelength of the specimen 10. The light exited from the coherent light source 1 is passed through the light intensity modulator 30, and converted into collimated light by the collector lens 2 to be incident on the ultrasonic wave spatial light modulator 3.

The light intensity modulator 30 is a light intensity modulator that modulates only an intensity of light exited from the coherent light source 1 in a time direction, without changing a wavefront shape of the light exited from the coherent light source 1. To the light intensity modulator 30, for example, an ultrasonic wave spatial light modulator that generates an ultrasonic traveling wave, an EO modulator that utilizes the Kerr effect, an EO modulator that utilizes the Pockels effect, a light-reducing filter or the like can be applied. The light intensity modulator 30 is controlled by the controlling device 19.

First, for easier understanding, the light intensity modulator 30 is assumed to be turned off. In this case, light that is incident on the ultrasonic wave spatial light modulator 3 maintains a certain level of intensity.

The ultrasonic wave spatial light modulator 3 has an ultrasonic wave propagation path R propagating an ultrasonic wave in a direction perpendicular to an optical axis, and gives, by generating a planar standing wave of ultrasonic wave (referred to as "ultrasonic standing wave", hereinafter) in the ultrasonic wave propagation path R, a refractive index distribution of sinusoidal shape to the ultrasonic wave propagation path R. Such an ultrasonic wave spatial light modulator 3 operates as a phase type diffraction grating with respect to the incident light, and branches the light into diffracted lights of respective orders (0th-order diffracted light, +first-order diffracted light, −first-order diffracted light, +second-order diffracted light, −second-order diffracted light, . . . ). Note that in FIG. 1, only 0th-order diffracted light and +first-order diffracted lights are illustrated as a representative. In FIG. 1, a solid line indicates the 0th-order diffracted light, and a dotted line indicates the ±first-order diffracted lights. The diffracted lights of respective orders exited from the ultrasonic wave spatial light modulator 3 pass through the lens 4, and then form a pupil conjugate plane.

Here, the pupil conjugate plane indicates a focal position of the lens 4 (rear focal position), and a position conjugated with a pupil P of the later-described objective lens 9 (position at which the ±first-order diffracted lights are condensed) via the lens 7 and the lens 6 (note that a position determined by a person skilled in the art by taking the design requirements such as aberration, vignetting and the like of the objective lens 9 and the lenses 6 and 7, also falls into the concept of "conjugate position").

The mask switching mechanism 5A is disposed in the vicinity of the pupil conjugate plane, and is a mechanism that switches a mask to be inserted into the pupil conjugate plane between a 0th-order light blocking mask 5A0 and a higher-order light blocking mask 5Ah.

The 0th-order light blocking mask 5A0 has a function of blocking 0th-order diffracted light and higher-order diffracted light of second-order or higher, and making only ±first-order diffracted lights (only two beams) pass through the mask, out of diffracted lights of respective orders which are incident on the pupil conjugate plane. The 0th-order light blocking mask 5A0 is obtained by forming a plurality of openings or transmitting portions on a substrate, and a position of the openings or the transmitting portions when the mask is inserted into an optical path corresponds to an area, on the pupil conjugate plane, through which the ±first-order diffracted lights pass.

The higher-order light blocking mask 5Ah has a function of blocking higher-order diffracted light of second-order or higher, and making only ±first-order diffracted lights and 0th-order diffracted light (only three beams) pass through the mask, out of diffracted lights of respective orders which are incident on the pupil conjugate plane. The higher-order light blocking mask 5Ah is obtained by forming a plurality of openings or transmitting portions on a substrate, and a position of the openings or the transmitting portions when the mask is inserted into the optical path corresponds to an area, on the pupil conjugate plane, through which the ±first-order diffracted lights and the 0th-order diffracted light pass.

Note that generally, there is a high possibility that an intensity of 0th-order diffracted light becomes larger than an intensity of ±first-order diffracted lights. However, in the present system, since both of the 0th-order diffracted light and the ±first-order diffracted lights are used for illumination, an intensity ratio of the 0th-order diffracted light, the +first-order diffracted light and the −first-order diffracted light directed toward the specimen 10 is desirably approximated as much as possible to 1:1:1. Accordingly, for example, a chromium film having a function of light-reducing filter or the like may be provided to the area, on the higher-order light blocking mask 5Ah, through which the 0th-order diffracted light passes. Further, it is also possible to previously optimize electric power to be applied to the ultrasonic wave spatial light modulator 3, in addition to the use of the light-reducing filter, in order to make the intensity ratio of the 0th-order diffracted light, the +first-order diffracted light and the −first-order diffracted light further approximate to 1:1:1.

Here, explanation will be made by assuming that only the former of the 0th-order light blocking mask 5A0 and the higher-order light blocking mask 5Ah is inserted into the optical path, as illustrated in FIG. 1. In this case, diffracted lights that pass through the mask switching mechanism 5A are only the ±first-order diffracted lights.

A conjugate plane of the specimen 10 is formed by the ±first-order diffracted lights passed through the 0th-order light blocking mask 5A0 of the mask switching mechanism 5A, via the lens 6. In the vicinity of the conjugate plane of the specimen 10, the field stop 5B is disposed, and the field stop 5B has a function of controlling a size of illuminated area (observational area) on the specimen 10.

The ±first-order diffracted lights passed through the field stop 5B pass through the lens 7, and after that, the lights are incident on the dichroic mirror 8 via the excitation filter 8a, and reflected by the dichroic mirror 8. The ±first-order diffracted lights reflected by the dichroic mirror 8 respectively form spots at mutually different positions on the pupil P of the objective lens 9. Note that the formation positions of the two spots formed by the ±first-order diffracted lights on the pupil P are at approximately an outermost peripheral portion of the pupil P, and positions symmetric to each other with respect to an optical axis of the objective lens 9. In this case, the ±first-order diffracted lights exited from the tip of the objective lens 9 illuminate the specimen 10 from mutually opposing directions at an angle corresponding to NA of the objective lens 9. Note that when one pitch of diffraction grating is changed just a little as a result of slightly changing a frequency of applied voltage, as will be described later, the formation positions of the two spots are extremely slightly changed.

Here, the ±first-order diffracted lights irradiated to the specimen 10 are mutually coherent lights exited from the coherent light source 1. Accordingly, by the ±first-order diffracted lights, striped interference fringes with a uniform fringe pitch are projected onto the specimen 10. Specifically, an illumination pattern with respect to the specimen 10 corresponds to an illumination pattern having a fringe structure. The illumination with the illumination pattern having the fringe structure as above is structured illumination. In the fluorescent area (fluorescent-stained area described above) of the specimen 10 subjected to the structured illumination, a fluorescent material is excited to generate fluorescence.

Note that only two beams of the ±first-order diffracted lights are used to realize the structured illumination, so that the illumination is structured in an in-plane direction of the specimen 10, but, it is not structured in a depth direction (optical axis direction) of the specimen 10. Hereinafter, such structured illumination is referred to as "two-beam structured illumination".

When the two-beam structured illumination is employed, a moiré fringe corresponding to a difference between a structural pitch of the two-beam structured illumination and a structural pitch of the fluorescent area (corresponding to a structural pitch of the specimen) appears on the specimen 10. On the moiré fringe, a spatial frequency of the structure of the fluorescent area is modulated to be shifted to a spatial frequency that is lower than the actual spatial frequency. Therefore, with the use of the two-beam structured illumination, even a fluorescence that exhibits a high component of spatial frequency in the structure of the fluorescent area, namely, a fluorescence emitted at a large angle that exceeds a resolution limit of the objective lens 9, can be incident on the objective lens 9.

The fluorescence that is emitted from the specimen 10 and incident on the objective lens 9 is converted into collimated light by the objective lens 9, and then incident on the dichroic mirror 8. The fluorescence transmits through the dichroic mirror 8, and then passes through the second objective lens 11 via the fluorescence filter 8b, to thereby form a fluorescent image of the specimen 10 on an imaging plane of the imaging device 12. Note that this fluorescent image includes not only structural information of the fluorescent area of the specimen 10 but also structural information of the two-beam structured illumination, and in this fluorescent image, the spatial frequency of the structure of the fluorescent area of the specimen 10 is still being modulated (namely, the spatial frequency is still being shifted to the spatial frequency that is lower than the actual spatial frequency).

The controlling device 19 controls the ultrasonic standing wave generated in the ultrasonic wave propagation path R of the ultrasonic wave spatial light modulator 3, to thereby change patterns of the two-beam structured illumination (details will be described later). Further, the controlling device 19 drives the imaging device 12 when the patterns of the two-beam structured illumination are under respective states to obtain a plurality of types of image data, and sequentially sends the plurality of types of image data to the image storing-calculating device 13. Note that a charge storage time per one frame in the imaging device 12 is, for example, 1/30 seconds, 1/60 seconds or the like.

The image storing-calculating device 13 performs separating calculation with the use of linear calculation on the plurality of types of image data which are taken therein, to thereby obtain image data as a result of removing the structural information of structured illumination. Further, the image storing-calculating device 13 performs demodulating calculation with the use of multiplication with a demodulation coefficient on the image data as a result of removing the structural information to obtain demodulated image data as a result of returning the spatial frequency of the structural information of the fluorescent area to the actual spatial frequency, and sends the demodulated image data to the image displaying device 14. Note that for concrete calculation, a method disclosed in, for example, Patent Document 3 can be employed. Accordingly, a resolved image that exceeds the resolution limit of the objective lens 9 (two-dimensional super-resolved image) is displayed on the image displaying device 14.

FIG. 2(A) is a schematic diagram illustrating a pattern of ultrasonic standing wave generated in the ultrasonic wave propagation path R, and FIG. 2(B) is a schematic diagram illustrating a pattern of two-beam structured illumination (arrangement of bright part and dark part) corresponding to the pattern (note that actually, only a pattern of area through which an effective light flux passes, out of the pattern of the ultrasonic standing wave, contributes to the pattern of the two-beam structured illumination). Further, in FIG. 2(A), a number of wave of the ultrasonic standing wave is set to "2", which is smaller than the actual number, for easier understanding of the explanation.

As illustrated in FIG. 2(A), when the number of wave of the ultrasonic standing wave (the number of wave is counted as one when the phase is shifted by $2\pi$) is "2", a number of fringe (number of bright part or dark part) of the two-beam structured illumination formed by the interference of ±first-order lights becomes "4", as illustrated in FIG. 2(B). Specifically, the number of fringe of the two-beam structured illumination becomes twice the number of wave of the ultrasonic standing wave corresponding to the number of fringe.

Further, when the number of wave of the ultrasonic standing wave is changed, by 1/2, in three ways such as 2, (2+1/2), and 3 (namely, when the wavelength of the ultrasonic standing wave is changed), as illustrated in FIG. 2(C), FIG. 2(D), and FIG. 2(E), for example, the number of fringe of the two-beam structured illumination corresponding to the number of wave is changed, by one, in three ways such as 4, 5, and 6.

Figure 2:
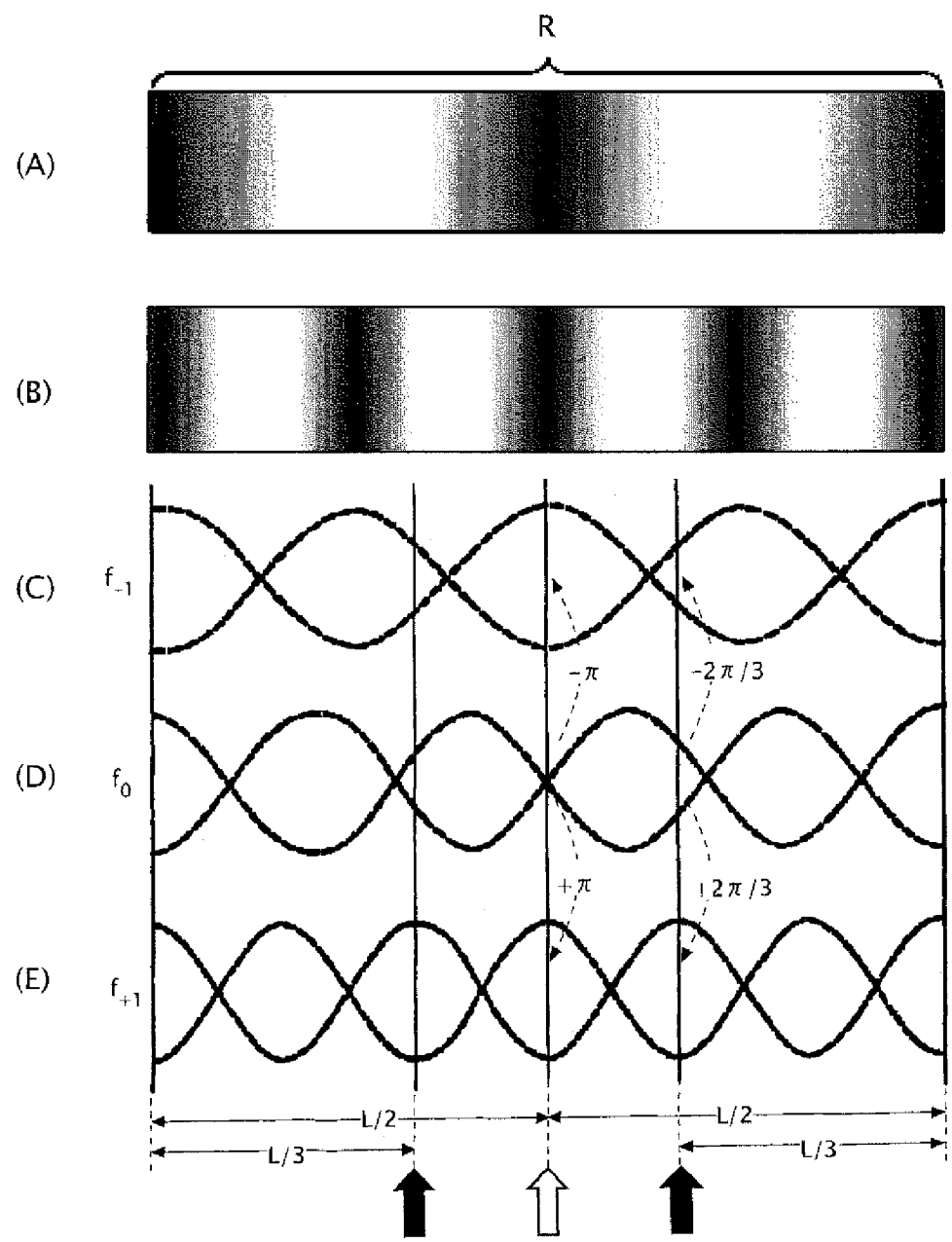
FIG. 2(A) is a schematic diagram illustrating a pattern of ultrasonic standing wave generated in an ultrasonic wave propagation path R of an ultrasonic wave spatial light modulator 3.
FIG. 2(B) is a schematic diagram illustrating a pattern of two-beam structured illumination (arrangement of bright part and dark part) corresponding to the pattern.
FIG. 2(C) to FIG. 2(E) are diagrams explaining a change in a number of fringe when a number of wave is changed.

Here, if attention is focused only on a portion deviated by 1/2 from one end of the ultrasonic wave propagation path R, as indicated by a white arrow mark in FIG. 2, the phase of the two-beam structured illumination corresponding to the focused portion is shifted, by "$\pi$", in three ways.

Further, if attention is focused only on portions each deviated by 1/3 from one end of the ultrasonic wave propagation path R, as indicated by black arrow marks in FIG. 2, the phase of the two-beam structured illumination corresponding to each of the focused portions is shifted, by "$2\pi/3$", in three ways.

Accordingly, if an incident area of light with respect to the ultrasonic wave propagation path R is tentatively limited only to the position indicated by the white arrow mark, the phase of the two-beam structured illumination can be shifted by "$\pi$", only by changing the number of wave of the ultrasonic standing wave by 1/2.

Further, if the incident area of light with respect to the ultrasonic wave propagation path R is tentatively limited only to the positions indicated by the black arrow marks, the phase of the two-beam structured illumination can be shifted by "$2\pi/3$", only by changing the number of wave of the ultrasonic standing wave by 1/2.

Here, the aforementioned separating calculation for removing the structural information of the two-beam structured illumination requires at least three pieces of image data with different phases of the two-beam structured illumination. In that case, it is only required to set an amount of phase shift per one step of the two-beam structured illumination to $2\pi/3$, for example.

At this time, in order to generate the two-dimensional super-resolved image by the two-beam structured illumination, a distance D from a center of spot (effective diameter) S of light which is incident on the ultrasonic wave propagation path R to one end of the ultrasonic wave propagation path R, may be set to one-third a length L in a propagation direction of the ultrasonic wave propagation path R (D=L/3), as illustrated in FIG. 3(A).

Figure 3:
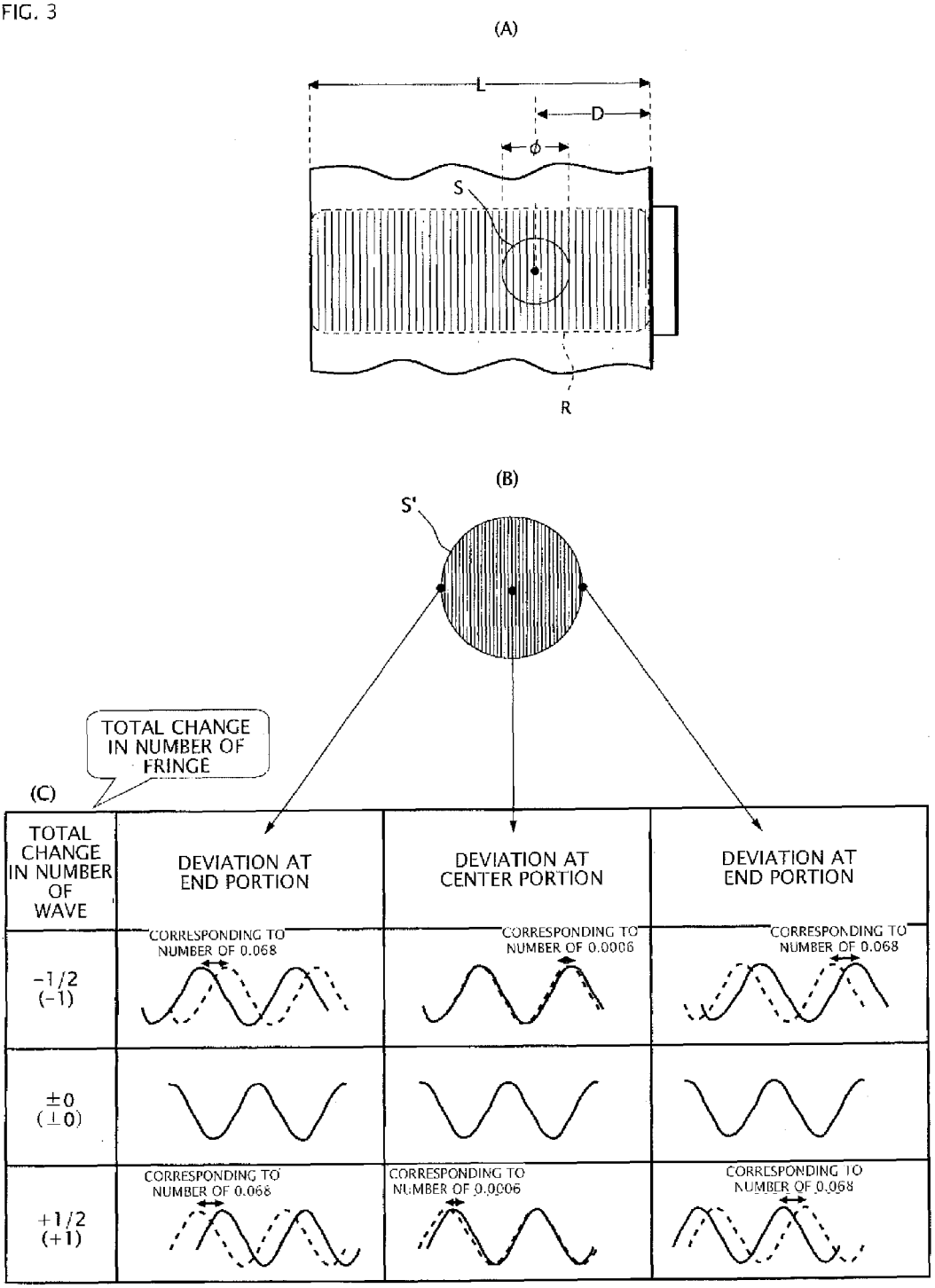
FIG. 3(A) is a diagram explaining a relation between a length L and a distance D.
FIG. 3(B) is a conceptual diagram of structured illumination S' corresponding to a spot S.
FIG. 3(C) is a diagram explaining a deviation of a number of fringe of the structured illumination S'.

However, when the number of wave of the ultrasonic standing wave generated in the ultrasonic wave propagation path R is changed by 1/2, the number of wave of the ultrasonic standing wave generated in the inside of the spot S is also deviated a little, so that the number of fringe of two-beam structured illumination S' corresponding to the spot S is also deviated a little, as illustrated in FIG. 3(B) (note that the pattern of wave and the pattern of fringe illustrated in FIG. 3 are illustrated in a schematic manner, and thus the number of wave and the number of fringe do not always coincide with the actual numbers).

Therefore, the length L of the ultrasonic wave propagation path R is set to be large enough, compared to a diameter $\phi$ of the spot S, so that the deviation of the number of fringe of the two-beam structured illumination S' can be regarded as approximately zero.

Concretely, the length L of the ultrasonic wave propagation path R and the diameter $\phi$ of the spot S are set to satisfy a relation of $\phi/L < \delta$, with respect to an acceptable amount $\delta$ of the deviation of the number of fringe of the two-beam structured illumination S'.

For example, if the deviation of the number of fringe of the two-beam structured illumination S' is required to be suppressed to the number of 0.15 or less, the relational expression becomes $\phi/L \leq 0.15$.

In the present embodiment, if the number of fringe is controlled at an appropriate frequency by setting that the diameter $\phi$ of the spot S is 4 mm and assuming that the length L of the ultrasonic wave propagation path R is 30 mm, the deviation of fringes at each of both ends of the two-beam structured illumination S' becomes one corresponding to about the number of 0.068, as illustrated in FIG. 3(C). For this reason, the deviation of the number of fringe in the entire area of the two-beam structured illumination S' can be suppressed to about the number of 0.068+0.068=0.13.

Note that in FIG. 3(C), a dotted line indicates an ideal pattern of the two-beam structured illumination S' (pattern when the deviation of the number of fringe is zero), a solid line indicates an actual pattern of the two-beam structured illumination S', and a deviation of the both is illustrated in an exaggerated manner for easier understanding.

Note that in the above explanation, the diameter $\phi$ of the spot S satisfies the relation of $\phi/L < \delta$ on the ultrasonic wave propagation path R of the ultrasonic wave spatial light modulator 3, but, it does not always have to satisfy the relation. For example, when the ±first-order diffracted lights exited from the ultrasonic wave spatial light modulator 3 are narrowed by the field stop 5B, the length L of the ultrasonic wave propagation path R, a diameter $\phi'$ of illuminated area (observational area, field area) on the specimen plane, and an optical power m from the specimen plane to the ultrasonic wave spatial light modulator 3, are only required to be set to satisfy a relation of $\phi' \times m/L < \delta$, with respect to the acceptable amount $\delta$ of the deviation of the number of fringe of the two-beam structured illumination S'.

FIG. 4(A) and FIG. 4(B) are diagrams specifically explaining a configuration of the ultrasonic wave spatial light modulator 3. FIG. 4(A) is a diagram in which the ultrasonic wave spatial light modulator 3 is seen from the front (optical axis direction), and FIG. 4(B) is a diagram in which the ultrasonic wave spatial light modulator 3 is seen from the side (direction perpendicular to the optical axis).

As illustrated in FIG. 4(A) and FIG. 4(B), the ultrasonic wave spatial light modulator 3 includes an acousto-optical medium 15, and the acousto-optical medium 15 is set to have a prismatic columnar shape having three pairs of mutually opposing parallel coupled side faces. Three transducers 18a, 18b, and 18c are individually provided on the three pairs of coupled side faces, on one side of each of the coupled side faces, and accordingly, three ultrasonic wave propagation paths are formed in one acousto-optical medium 15. Hereinafter, the ultrasonic wave propagation path formed between a formation face of the transducer 18a and a side face 15a opposing the formation face is set to an "ultrasonic wave propagation path Ra", the ultrasonic wave propagation path formed between a formation face of the transducer 18b and a side face 15b opposing the formation face is set to an "ultrasonic wave propagation path Rb", and the ultrasonic wave propagation path formed between a formation face of the transducer 18c and a side face 15c corresponding to the formation face is set to an "ultrasonic wave propagation path Rc".

Note that a material of the acousto-optical medium 15 is, for example, a quartz glass, a tellurite glass, a dense flint glass, a flint glass or the like, and the three pairs of coupled side faces and two bottom faces of the acousto-optical medium are respectively polished with sufficient precision.

Here, it is assumed that lengths L of the respective three ultrasonic wave propagation paths Ra, Rb, and Rc are common (L=30 mm). Further, the length L satisfies the aforementioned condition with respect to the diameter $\phi$ of the spot S described above. Further, the three ultrasonic wave propagation paths Ra, Rb, and Rc intersect at angles different by 60° from each other, at a position separated by L/3 from one end of each of the paths. At a position of the intersection, a center of the above-described spot S is positioned.

The transducer 18a is an ultrasonic wave transducer having a piezoelectric body 16a and two electrodes 17a individually formed on upper and lower faces of the piezoelectric body 16a, and is joined to one side face of the acousto-optical medium 15 via the electrode 17a being one of the two electrodes 17a. When an AC voltage of high frequency with sinusoidal shape is applied between the two electrodes 17a of the transducer 18a, the piezoelectric body 16a vibrates in a thickness direction, resulting in that a planar ultrasonic wave reciprocates in the ultrasonic wave propagation path Ra. When the frequency of AC voltage applied between the two electrodes 17a is set to a specific frequency (appropriate frequency), the ultrasonic wave becomes a standing wave, so that a distribution of sinusoidal shape is given to a refractive index of the ultrasonic wave propagation path, over a propagation direction of the ultrasonic wave. Accordingly, the ultrasonic wave propagation path Ra becomes a phase type diffraction grating having a phase grating perpendicular to the propagation direction of the ultrasonic wave. Hereinafter, the propagation direction in the ultrasonic wave propagation path Ra is referred to as a "first direction".

Further, the transducer 18b, which also has the same configuration as that of the transducer 18a, has a piezoelectric body 16b and two electrodes 17b individually formed on upper and lower faces of the piezoelectric body 16b, and is joined to one side face of the acousto-optical medium 15 via the electrode 17b being one of the two electrodes 17b.

Therefore, when an AC voltage of appropriate frequency is applied between the two electrodes 17b of the transducer 18b, a planar ultrasonic wave propagates in the ultrasonic wave propagation path Rb, so that the ultrasonic wave propagation path Rb becomes a phase type diffraction grating having a phase grating perpendicular to the propagation direction of the ultrasonic wave. Hereinafter, the propagation direction in the ultrasonic wave propagation path Rb is referred to as a "second direction". This second direction makes an angle of 60° with the first direction.

Further, the transducer 18c, which also has the same configuration as that of the transducer 18a, has a piezoelectric body 16c and two electrodes 17c individually formed on upper and lower faces of the piezoelectric body 16c, and is joined to one side face of the acousto-optical medium 15 via the electrode 17c being one of the two electrodes 17c.

Therefore, when an AC voltage of appropriate frequency is applied between the two electrodes 17c of the transducer 18c, a planar ultrasonic wave propagates in the ultrasonic wave propagation path Rc, so that the ultrasonic wave propagation path Rc becomes a phase type diffraction grating having a phase grating perpendicular to the propagation direction of the ultrasonic wave. Hereinafter, the propagation direction in the ultrasonic wave propagation path Rc is referred to as a "third direction". This third direction makes an angle of −60° with the first direction.

Figure 5:
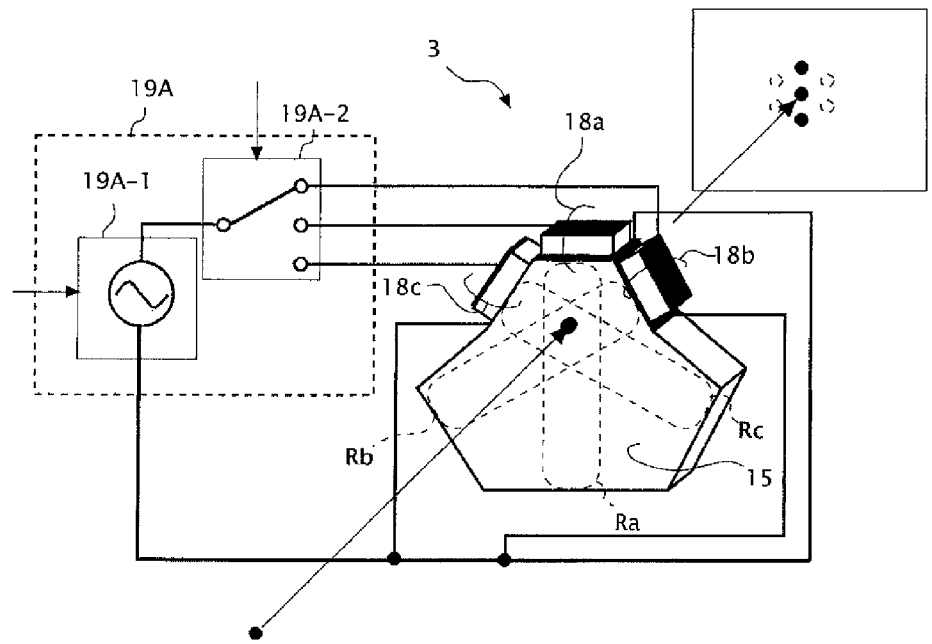
FIG. 5 is a diagram explaining a basic configuration of a controlling device 19 (driving circuit 19A).

FIG. 5 is a diagram explaining a basic configuration of the controlling device 19. A reference numeral 19A in FIG. 5 denotes a driving circuit 19A included in the controlling device 19, and the driving circuit 19A includes a high-frequency AC power source 19A-1 and a selector switch 19A-2.

The high-frequency AC power source 19A-1 generates an AC voltage to be supplied to the ultrasonic wave spatial light modulator 3. A frequency of the AC voltage is controlled to an appropriate frequency (any value within a range of several tens of MHz to 100 MHz, for example), by a CPU in the controlling device 19.

Therefore, when the amount of phase shift of the two-beam structured illumination S' is changed in steps, in three ways of $-2\pi/3$, 0, and $+2\pi/3$, for example, the CPU may switch the frequency of the AC voltage among three ways of different appropriate frequencies $f_{-1}$, $f_0$, and $f_{+1}$.

For example, the appropriate frequency $f_0$ is set to an appropriate frequency (80 MHz) for generating ultrasonic standing waves whose number is 100 (the number of fringe of the two-beam structured illumination corresponding thereto is 200) in the ultrasonic wave propagation paths Ra, Rb, and Rc each having the length L of 30 mm. With the use of the appropriate frequency $f_0$, the amount of phase shift of the two-beam structured illumination S' is zero.

In this case, the appropriate frequency $f_{-1}$ becomes an appropriate frequency (79.946 MHz) for generating ultrasonic standing waves whose number is (100−1/2) (the number of fringe of the two-beam structured illumination corresponding thereto is 199) in the ultrasonic wave propagation paths Ra, Rb, and Rc each having the length L of 30 mm. With the use of the appropriate frequency $f_{-1}$, the amount of phase shift of the two-beam structured illumination S' becomes $-2\pi/3$.

Further, the appropriate frequency $f_{+1}$ becomes an appropriate frequency (80.054 MHz) for generating ultrasonic standing waves whose number is (100+1/2) (the number of fringe of the two-beam structured illumination corresponding thereto is 201) in the ultrasonic wave propagation paths Ra, Rb, and Rc each having the length L of 30 mm. With the use of the appropriate frequency $f_{+1}$, the amount of phase shift of the two-beam structured illumination S' becomes $+2\pi/3$.

The selector switch 19A-2 is disposed between the high-frequency AC power source 19A-1 and the ultrasonic wave spatial light modulator 3, and can switch a connection destination on the side of the ultrasonic wave spatial light modulator 3, among the three transducers 18a, 18b, and 18c of the ultrasonic wave spatial light modulator 3. The connection destination of the switch 19A-2 is appropriately switched by the CPU in the controlling device 19.

When the connection destination of the selector switch 19A-2 is on the side of the transducer 18a, the AC voltage is applied between the two electrodes of the transducer 18a, so that only the ultrasonic wave propagation path Ra among the three ultrasonic wave propagation paths Ra, Rb, and Rc, becomes effective.

Further, when the connection destination of the selector switch 19A-2 is on the side of the transducer 18b, the AC voltage is applied between the two electrodes of the transducer 18b, so that only the ultrasonic wave propagation path Rb among the three ultrasonic wave propagation paths Ra, Rb, and Rc, becomes effective.

Further, when the connection destination of the selector switch 19A-2 is on the side of the transducer 18c, the AC voltage is applied between the two electrodes of the transducer 18c, so that only the ultrasonic wave propagation path Rc among the three ultrasonic wave propagation paths Ra, Rb, and Rc, becomes effective.

As above, when the effective ultrasonic wave propagation path is switched among the three ultrasonic wave propagation paths Ra, Rb, and Rc, the direction of two-beam structured illumination S' can be switched among a direction corresponding to the first direction, a direction corresponding to the second direction, and a direction corresponding to the third direction.

Accordingly, by appropriately driving the above-described ultrasonic wave spatial light modulator 3 and controlling device 19, it is possible to generate a detailed two-dimensional super-resolved image. Concrete explanation will be made hereinbelow.

Figure 6:
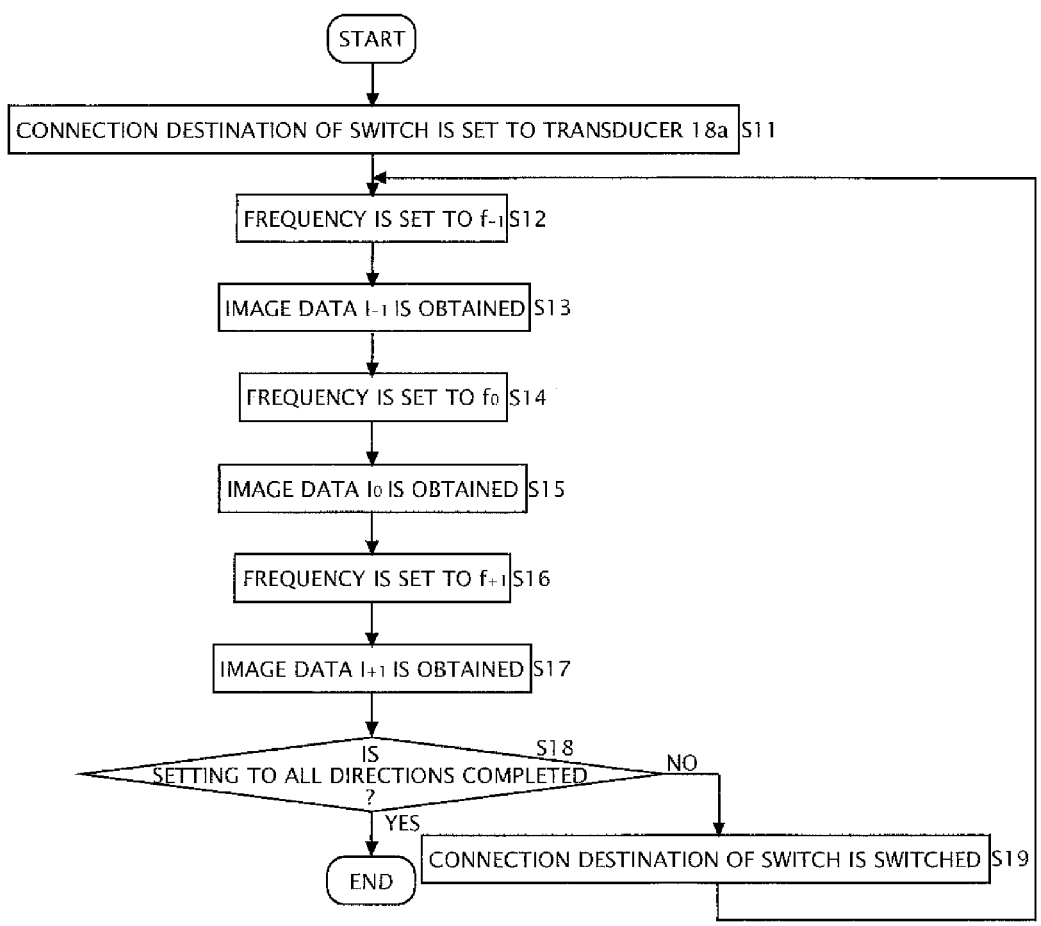
FIG. 6 is an operational flow chart of a CPU in a two-dimensional mode.

FIG. 6 is an operational flow chart of the CPU. Hereinafter, respective steps will be described in order.

Step S11: The CPU sets the connection destination of the selector switch 19A-2 to a first transducer (transducer 18a) side, to thereby set the direction of two-beam structured illumination S' to the direction corresponding to the first direction.

Step S12: The CPU sets the frequency of AC voltage generated by the high-frequency AC power source 19A-1 to the appropriate frequency $f_{-1}$, to thereby set the amount of phase shift of the two-beam structured illumination S' to $-2\pi/3$.

Step S13: The CPU drives the imaging device 12 under this state to obtain image data $I_{-1}$.

Step S14: The CPU sets the frequency of AC voltage generated by the high-frequency AC power source 19A-1 to the appropriate frequency $f_0$, to thereby set the amount of phase shift of the two-beam structured illumination S' to zero.

Step S15: The CPU drives the imaging device 12 under this state to obtain image data $I_0$.

Step S16: The CPU sets the frequency of AC voltage generated by the high-frequency AC power source 19A-1 to the appropriate frequency $f_{+1}$, to thereby set the amount of phase shift of the two-beam structured illumination S' to $+2\pi/3$.

Step S17: The CPU drives the imaging device 12 under this state to obtain image data $I_{+1}$.

Step S18: The CPU judges whether or not the setting of direction of the two-beam structured illumination S' to all of the above-described three directions is completed, in which when the setting is not completed, the process proceeds to step S19, and when the setting is completed, the flow is terminated.

Step S19: The CPU switches the direction of two-beam structured illumination S' by switching the connection destination of the selector switch 19A-2, and then the process proceeds to step S12.

According to the above-described flow, pieces of image data $Ia_{-1}$, $Ia_0$, and $Ia_{+1}$ regarding the first direction, pieces of image data $Ib_{-1}$, $Ib_0$, and $Ib_{+1}$ regarding the second direction, and pieces of image data $Ic_{-1}$, $Ic_0$, and $Ic_{+1}$ regarding the third direction are obtained. These pieces of image data are taken into the image storing-calculating device 13.

The image storing-calculating device 13 obtains demodulated image data Ia' along the first direction based on the three pieces of image data $Ia_{-1}$, $Ia_0$, and $Ia_{+1}$ regarding the first direction, obtains demodulated image data Ib' along the second direction based on the three pieces of image data $Ib_{-1}$, $Ib_0$, and $Ib_{+1}$ regarding the second direction, and obtains demodulated image data Ic' along the third direction based on the three pieces of image data $Ic_{-1}$, $Ic_0$, and $Ic_{+1}$ along the third direction. After that, the image storing-calculating device 13 combines the three pieces of demodulated image data Ia', Ib', and Ic' on a wave number space, then returns the resultant to the real space again to obtain image data I of super-resolved image along the first direction, the second direction, and the third direction, and sends the image data I to the image displaying device 14. The super-resolved image corresponds to a two-dimensional super-resolved image along the three directions in the in-plane direction of the specimen 10.

As described above, in the present system, by turning off the light intensity modulator 30 and inserting the 0th-order light blocking mask 5A0 into the pupil conjugate plane, it is possible to realize the structured illumination formed of the ±first-order diffracted lights (specifically, the two-beam structured illumination).

Accordingly, in the present system, by obtaining the plurality of pieces of image data by switching the patterns of the two-beam structured illumination, it becomes possible to generate the super-resolved image along the in-plane direction of the specimen 10 (specifically, the two-dimensional super-resolved image). Hereinafter, a mode of the present system for generating the two-dimensional super-resolved image is referred to as a "two-dimensional mode".

Further, in the present system, by turning on the light intensity modulator 30 and inserting the higher-order light blocking mask 5Ah into the pupil conjugate plane, it is possible to realize structured illumination formed of the ±first-order diffracted lights and the 0th-order diffracted light (specifically, three-beam structured illumination).

Accordingly, in the present system, by obtaining a plurality of pieces of image data by switching patterns of the three-beam structured illumination, it becomes possible to generate a super-resolved image along the in-plane direction and the optical axis direction of the specimen 10 (specifically, a three-dimensional super-resolved image). Hereinafter, a mode of the present system for generating the three-dimensional super-resolved image is referred to as a "three-dimensional mode".

Hereinafter, the three-dimensional mode will be described in detail. Note that here, only a point of difference between the three-dimensional mode and the above-described two-dimensional mode will be described.

The three-beam structured illumination projected onto the specimen 10 in the three-dimensional mode is formed of three beams of the ±first-order diffracted lights and the 0th-order diffracted light, so that the illumination is structured not only in the in-plane direction of the specimen 10 but also in the optical axis direction of the specimen 10. Besides, a pattern of the three-beam structured illumination in the in-plane of the specimen 10 is slightly different from the pattern of the two-beam structured illumination in the in-plane of the specimen 10. This point will be described in detail hereinafter.

Figure 7:
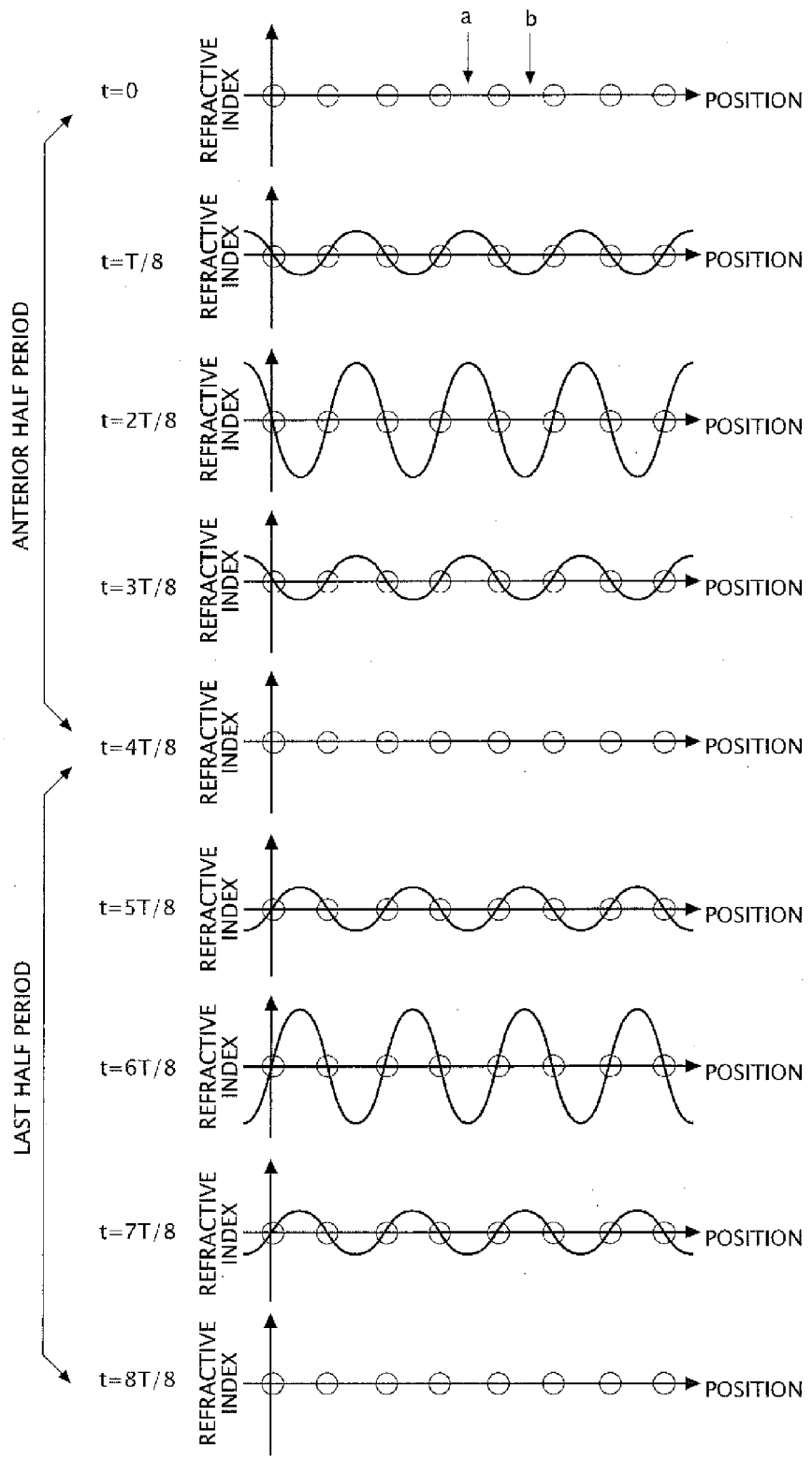
FIG. 7 is a diagram illustrating a time-variation of a refractive index distribution of an ultrasonic wave propagation path.

First, the ultrasonic standing wave is generated in the ultrasonic wave spatial light modulator 3 as described above, and an instantaneous value of a pattern of the ultrasonic standing wave (=refractive index distribution of ultrasonic wave propagation path) is time-varied, from an upper direction to a lower direction in FIG. 7.

In FIG. 7, a time t at a moment at which the refractive index distribution of the ultrasonic wave propagation path becomes flat is set to t=0, and a time-variable pitch of the refractive index distribution is set to T. Incidentally, the pitch T corresponds to a reciprocal of a frequency of an AC voltage supplied to the ultrasonic wave spatial light modulator 3. Hereinafter, a period of time of t=0 to T/2 is referred to as an "anterior half period of the refractive index variation", and a period of time of t=T/2 to T is referred to as a "last half period of the refractive index variation". Further, as indicated by a circle mark in FIG. 7, a portion in which the refractive index is not varied in the ultrasonic wave propagation path is referred as a "node", and a portion in which the refractive index is varied is referred to as an "antinode".

Here, if attention is focused on an antinode a in FIG. 7, it can be understood that a refractive index of the antinode a becomes higher than a refractive index of a node (the medium becomes dense) in the anterior half period of the refractive index variation, but, the refractive index of the antinode a becomes lower than the refractive index of the node (the medium becomes coarse) in the last half period of the refractive index variation.

On the other hand, if attention is focused on an antinode b adjacent to the antinode a in FIG. 7, it can be understood that a refractive index of the antinode b becomes lower than a refractive index of the node (the medium becomes coarse) in the anterior half period of the refractive index variation, but, the refractive index of the antinode b becomes higher than the refractive index of the node (the medium becomes dense) in the last half period of the refractive index variation.

Figure 8:
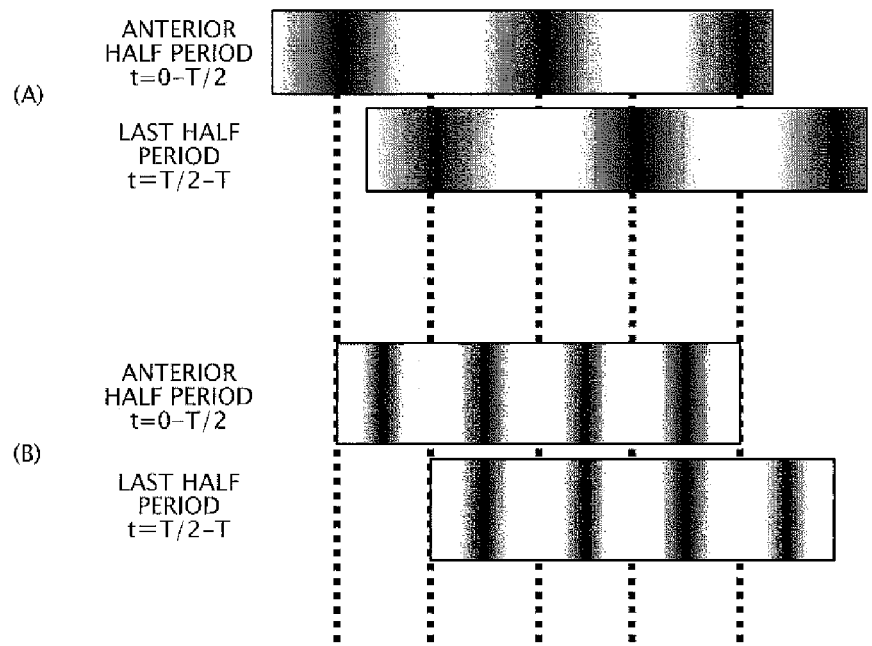
FIG. 8(A) is a schematic diagram illustrating a pattern of ultrasonic standing wave.
FIG. 8(B) is a schematic diagram illustrating a pattern of two-beam structured illumination.
Figure 9:
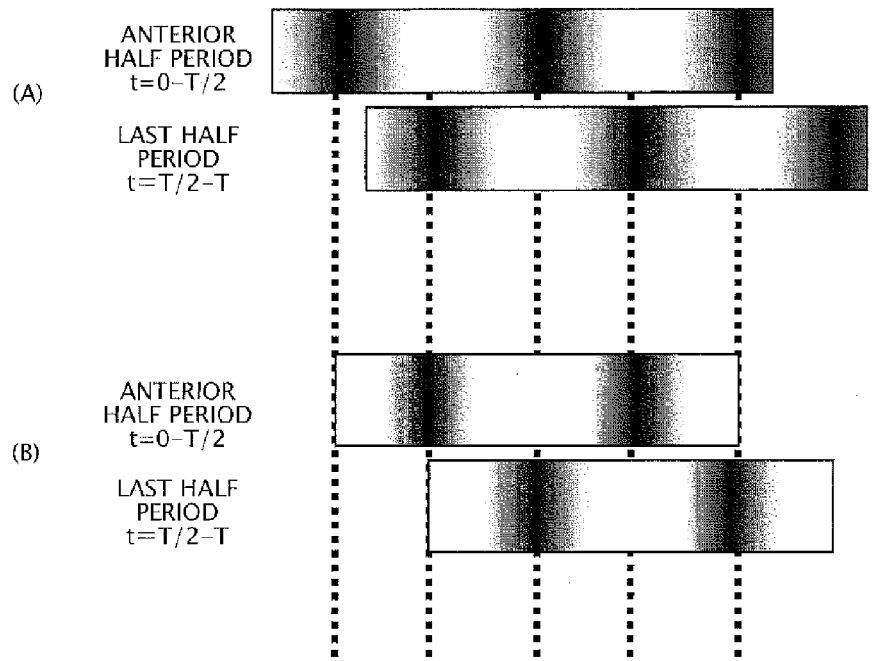
FIG. 9(A) is a schematic diagram illustrating a pattern of ultrasonic standing wave.
FIG. 9(B) is a schematic diagram illustrating a pattern of three-beam structured illumination.

Accordingly, if the ultrasonic wave spatial light modulator 3 is regarded as a phase type diffraction grating, a phase distribution of the phase type diffraction grating is reversed between the anterior half period and the last half period of the refractive index variation, as illustrated in FIG. 8(A) or FIG. 9(A). Specifically, the phase type diffraction grating is laterally shifted by a half grating pitch, between the anterior half period and the last half period of the refractive index variation.

Here, the two-beam structured illumination is formed of two-beam interference fringes, so that the number of fringe on the specimen 10 of the two-beam structured illumination is twice the number of grating of the phase type diffraction grating corresponding thereto, as schematically illustrated in FIG. 8(B). Accordingly, when the phase type diffraction grating is laterally shifted as illustrated in FIG. 8(A), the pattern of the two-beam structured illumination is changed as illustrated in FIG. 8(B). Specifically, in the two-beam structured illumination, a lateral displacement occurs by an amount corresponding to one pitch of fringe, between the anterior half period and the last half period of the refractive index variation.

Therefore, when the two-beam structured illumination is subjected to time integration over a period of time which is long enough compared to the pitch T, patterns at respective time points of the two-beam structured illumination are emphasized, resulting in that a high-contrast striped image is obtained. In this case, imaging of the two-beam structured illumination can be realized by the imaging device 12.

On the other hand, the three-beam structured illumination is formed of three-beam interference fringes, so that the number of fringe on the specimen 10 of the three-beam structured illumination becomes one time the number of grating of the phase type diffraction grating corresponding thereto, as schematically illustrated in FIG. 9(B). Accordingly, when the phase type diffraction grating is laterally shifted as illustrated in FIG. 9(A), the pattern of the three-beam structured illumination is changed as illustrated in FIG. 9(B). Specifically, in the three-beam structured illumination, a lateral displacement occurs by an amount corresponding to a half pitch of fringe, between the anterior half period and the last half period of the refractive index variation.

Therefore, when the three-beam structured illumination is subjected to time integration over a period of time which is long enough compared to the pitch T, patterns at respective time points of the three-beam structured illumination cancel each other, resulting in that a uniform image with no contrast (gray image) is obtained. In this case, imaging of the three-beam structured illumination cannot be realized by the imaging device 12.

The reason why the light intensity modulator 30 (refer to FIG. 1) is provided in the present system is for solving this problem (problem regarding the reduction in contrast) in the three-dimensional mode.

Figure 10:
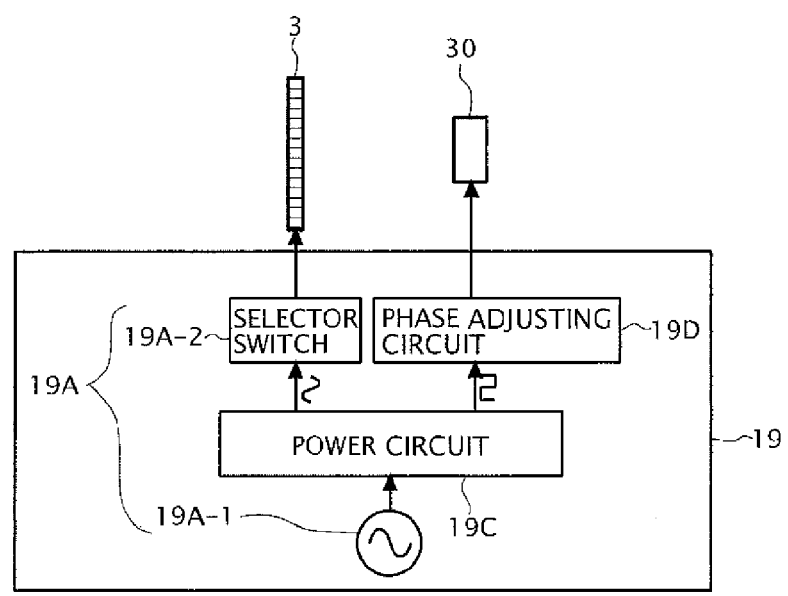
FIG. 10 is a diagram explaining a configuration of a controlling device 19 related to a three-dimensional mode.

FIG. 10 is a diagram explaining a configuration of a controlling device 19 regarding the three-dimensional mode. As illustrated in FIG. 10, the controlling device 19 includes a power circuit 19C, a phase adjusting circuit 19D and the like, in addition to the above-described AC power source 19A-1 and selector switch 19A-2.

The power circuit 19C has a first output terminal and a second output terminal, in which the first output terminal is a terminal for supplying the aforementioned AC voltage (sine signal) to the side of the ultrasonic wave spatial light modulator 3, and the second output terminal is a terminal for supplying a pulse voltage (pulse signal) to the side of the light intensity modulator 30.

The power circuit 19C constantly makes a frequency of the pulse signal output from the second output terminal coincide with a frequency of the sine signal output from the first output terminal, and when the frequency of the sine signal is switched by a CPU in the controlling device 19, the frequency of the pulse signal is also switched in a similar manner. Note that a duty ratio (ON period/pulse period) of the pulse signal is set to a previously determined ratio (which is set to 1/2, in this case), and is unchanged without depending on the frequency of the pulse signal.

The phase adjusting circuit 19D is interposed between the power circuit 19C and the light intensity modulator 30, and adjusts, in accordance with an instruction from the CPU in the controlling device 19, a phase relationship between the sine signal and the pulse signal.

Figure 11A:
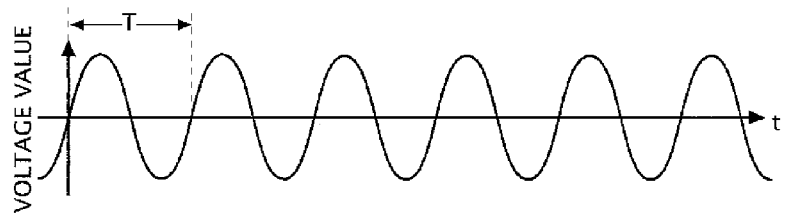
FIG. 11A is a diagram illustrating a waveform of sine signal output from a first output terminal.
Figure 11B:
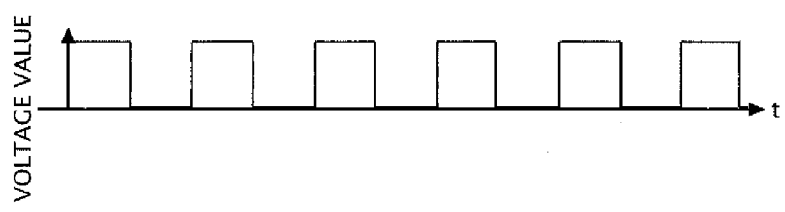
FIG. 11B is a diagram illustrating a waveform of pulse signal output from a second output terminal.

FIG. 11A is a diagram illustrating a waveform of the sine signal, and FIG. 11B is a diagram illustrating a waveform of the pulse signal. Out of the above, the waveform of the sine signal defines a waveform of time-variation of the ultrasonic standing wave in the ultrasonic wave spatial light modulator 3 (specifically, a waveform of time-variation of refractive index of each of the antinodes a and b), and the waveform of the pulse signal defines a waveform of time-variation of an intensity of incident light with respect to the ultrasonic wave spatial light modulator 3.

Accordingly, when the CPU in the controlling device 19 optimizes a phase adjusting amount of the phase adjusting circuit 19D, a period of time during which light is incident on the ultrasonic wave spatial light modulator 3, can be limited only to either the anterior half period or the last half period of the refractive index variation described above. When such an appropriate control is conducted, it is possible to prevent the patterns at respective time points of the three-beam structured illumination from cancelling each other, resulting in that the contrast of the image of the three-beam structured illumination can be maximized.

Accordingly, in advance of the three-dimensional mode, the CPU in the controlling device 19 continuously drives each of the coherent light source 1, the imaging device 12, and the phase adjusting circuit 19D in a state where a uniform test specimen, in place of the specimen 10, is disposed in the present system, changes a phase adjusting amount of the light intensity modulator 30 while referring to a contrast of an image output from the imaging device 12, and fixes the phase adjusting amount at a time point at which the contrast becomes maximum (or at a time point at which the contrast reaches a value equal to or greater than a threshold value).

FIG. 12 are diagrams each comparing a waveform of time-variation of the refractive index of an antinode a of the ultrasonic standing wave and a waveform of time-variation of an intensity of incident light. In FIG. 12, the waveform of time-variation of the refractive index of the antinode a is indicated by a solid line, and the waveform of time-variation of the intensity of incident light is indicated by a dotted line.

Figure 12A:
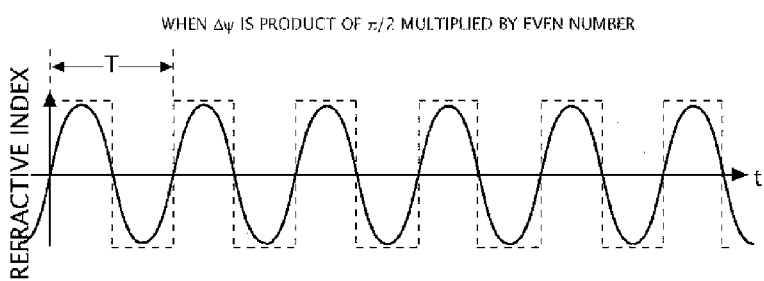
FIG. 12A, FIG. 12B, and FIG. 12C are diagrams each comparing a waveform of time-variation of a refractive index of antinode a of an ultrasonic standing wave (solid line) and a waveform of time-variation of an intensity of incident light (dotted line).

As illustrated in FIG. 12A, when a phase difference $\Delta\Psi$ between the waveform of time-variation of the refractive index of the antinode a and the waveform of time-variation of the intensity of incident light coincides with a product of $\pi/2$ multiplied by an even number, the period of time during which the incident light is incident is limited only to either the anterior half period or the last half period of the refractive index variation, so that the contrast of the image of the three-beam structured illumination becomes maximum.

Figure 12B:
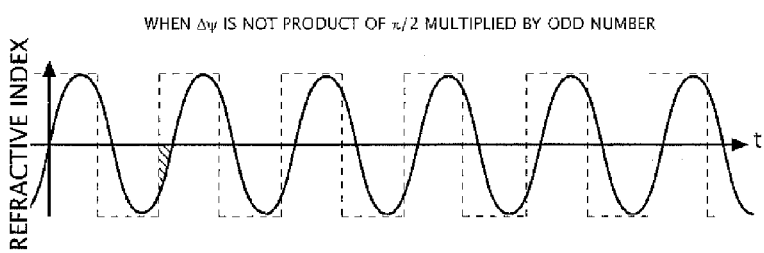

Further, as illustrated in FIG. 12B, even if the phase difference $\Delta\Psi$ between the waveform of time-variation of the refractive index of the antinode a and the waveform of time-variation of the intensity of incident light does not coincide with the product of $\pi/2$ multiplied by an even number, the image of the three-beam structured illumination has a contrast, as long as the phase difference $\Delta\Psi$ does not coincide with a product of $\pi/2$ multiplied by an odd number.

Figure 12C:
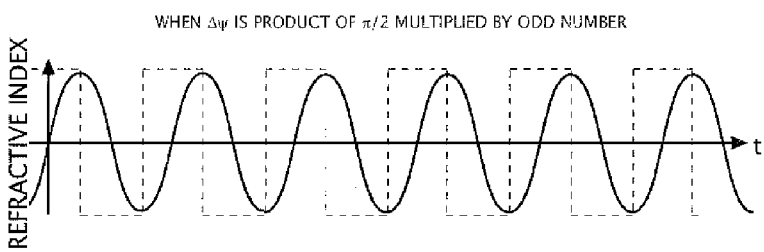

However, as illustrated in FIG. 12C, when the phase difference $\Delta\Psi$ between the waveform of time-variation of the refractive index of the antinode a and the waveform of time-variation of the intensity of incident light coincides with the product of $\pi/2$ multiplied by an odd number, the contrast of the image of the three-beam structured illumination becomes zero.

Therefore, in the three-dimensional mode, the phase difference $\Delta\Psi$ between the waveform of time-variation of the refractive index of the antinode a and the waveform of time-variation of the intensity of incident light is set to a product other than the product of $\pi/2$ multiplied by an odd number, and is desirably set to the product of $\pi/2$ multiplied by an even number.

Note that although the description is made here by focusing attention on the refractive index of the antinode a, the waveform of time-variation of the refractive index of the antinode b corresponds to the waveform of time-variation of the refractive index of the antinode a in which the phase is made to be opposite, so that the same also applies to a case where attention is focused on the refractive index of the antinode b.

Further, similar to the CPU in the two-dimensional mode (refer to FIG. 6), the CPU in the three-dimensional mode switches a connection destination of the selector switch 19A-2, to thereby switch a direction of the three-beam structured illumination among a first direction, a second direction, and a third direction.

Further, similar to the CPU in the two-dimensional mode (refer to FIG. 6), the CPU in the three-dimensional mode repeatedly obtains pieces of image data while shifting the phase of the three-beam structured illumination in respective cases where the direction of the three-beam structured illumination is the first direction, the second direction, and the third direction.

Note that in the three-dimensional mode, at least five pieces of image data with different phases of the three-beam structured illumination are required for the separating calculation for removing the structural information of the three-beam structured illumination (incidentally, it is sufficient if there are provided at least three pieces of image data in the two-dimensional mode).

For this reason, it is desirable that the CPU in the three-dimensional mode sets the amount of phase shift per one step in the three-beam structured illumination to $2\pi/5$, for example.

In that case, it is only required to set a distance D from a center of spot (effective diameter) S of light which is incident on the ultrasonic wave propagation path R to one end of the ultrasonic wave propagation path R, to one-fifth a length L in a propagation direction of the ultrasonic wave propagation path R (D=L/5).

Further, the CPU in the three-dimensional mode obtains five pieces of image data having amounts of phase shift which are different by $2\pi/5$, with respect to the respective directions, and sends the five pieces of image data regarding the first direction, the five pieces of image data regarding the second direction, and the five pieces of image data regarding the third direction to the image storing-calculating device 13.

Further, the image storing-calculating device 13 in the three-dimensional mode obtains demodulated image data along the first direction and the optical axis direction based on the five pieces of image data regarding the first direction, obtains demodulated image data along the second direction and the optical axis direction based on the five pieces of image data regarding the second direction, and obtains demodulated image data along the third direction and the optical axis direction based on the five pieces of image data regarding the third direction. After that, the image storing-calculating device 13 combines the three pieces of demodulated image data on a wave number space, then returns the resultant to the real space again to obtain image data of super-resolved image along the first direction, the second direction, the third direction, and the optical axis direction, and sends the image data to the image displaying device 14. The super-resolved image corresponds to a super-resolved image along the three directions in the in-plane of the specimen 10 and the optical axis direction of the specimen 10 (three-dimensional super-resolved image) (the above is the explanation of the three-dimensional mode). For the concrete calculation, a method disclosed in Patent Document 3, for example, can be employed.

As described above, in the present system, the length L of the ultrasonic wave propagation path R, the diameter $\phi$ of the spot S, and the distance D from one end of the ultrasonic wave propagation path R to the center of the spot S, are set to satisfy the optimum relation described above, so that the phase of the two-beam structured illumination or the three-beam structured illumination can be switched only by electrically switching the frequency of AC voltage given to the ultrasonic wave spatial light modulator 3. A period of time required for the switching is short, and can be reduced to 10 ms or less even including a time constant of the circuit system including the power source.

Therefore, a period of time taken for obtaining the required number of image data in the present system can be particularly reduced to a short period of time, when compared to a case where the optical element or the specimen 10 is mechanically moved for switching the phase of the two-beam structured illumination or the three-beam structured illumination.

Further, in the present system, there is no need to mechanically move the optical element or the specimen 10 for switching the phase of the two-beam structured illumination or the three-beam structured illumination, so that the configuration of the periphery of the optical system can be simplified.

Further, in the present system, the three ultrasonic wave propagation paths Ra, Rb, and Rc with different angles are formed in one acousto-optical medium 15, so that the direction of the two-beam structured illumination or the three-beam structured illumination can be switched only by electrically changing the connection state of the selector switch 19A-2. A period of time required for the switching is short, and can be reduced to 10 ms or less even including a time constant of the circuit system including the power source.

Therefore, a period of time taken for obtaining the required number of image data in the present system can be particularly reduced to a short period of time, when compared to a case where the optical element or the specimen 10 is mechanically rotated for switching the direction of the two-beam structured illumination or the three-beam structured illumination.

Further, in the present system, since the ultrasonic wave spatial light modulator is used as the phase type diffraction grating for generating the three-beam structured illumination, there is a possibility that the contrast of the image of the three-beam structured illumination becomes zero (a possibility that the imaging cannot be realized). However, in the three-dimensional mode of the present system, the light intensity modulator is used to modulate the intensity of incident light with respect to the ultrasonic wave spatial light modulator at an appropriate frequency, so that such a problem (problem regarding the reduction in contrast) can be avoided.

[Supplement Regarding Two-Dimensional Mode]

Note that in the two-dimensional mode of the present system, the change pattern of frequency of the AC voltage given to the transducer is set to a pattern in which the number of wave of the ultrasonic standing wave is changed by 1/2, and the distance D from the center of the spot (effective diameter) S to one end of the ultrasonic wave propagation path is set to one-third the length L in the propagation direction of the ultrasonic wave propagation path R (D=L/3) in order to set the phase shift pitch of the two-beam structured illumination in each of the first direction, the second direction and the third direction to $2\pi/3$, but, the present invention is not limited to this.

Concretely, the ultrasonic wave propagation path is only required to satisfy the following conditions.

First, the change pattern of frequency of the AC voltage given to the transducer is only required to be a pattern in which the number of wave of the ultrasonic standing wave is changed by M/2 (where |M| is an integer of 1 or more).

In that case, in order to set the phase shift pitch of the two-beam structured illumination to an arbitrary value $\Delta\psi$, the distance D from one end of the ultrasonic wave propagation path to the center of the spot S, and the total length L of the ultrasonic wave propagation path are only required to satisfy a relation of D:L=$\Delta\psi$/M:$2\pi$.

Incidentally, if it is set that M=1, the number of ultrasonic standing wave is changed only by 1/2, so that the deviation occurred, due to the change, in the number of fringe of the two-beam structured illumination can be minimized.

Further, when the number of image data used for the separating calculation is k, if it is set that $\Delta\psi=2\pi/k$, it is possible to securely obtain the required image data. Note that it is preferable that |k| is an integer of 3 or more.

[Supplement Regarding Three-Dimensional Mode]

Further, in the three-dimensional mode of the present system, the change pattern of frequency of the AC voltage given to the transducer is set to a pattern in which the number of wave of the ultrasonic standing wave is changed by 1/2, and the distance D from the center of the spot (effective diameter) S to one end of the ultrasonic wave propagation path is set to one-fifth the length L in the propagation direction of the ultrasonic wave propagation path R (D=L/5) in order to set the phase shift pitch of the three-beam structured illumination in each of the first direction, the second direction and the third direction to $2\pi/5$, but, the present invention is not limited to this.

Concretely, the ultrasonic wave propagation path is only required to satisfy the following conditions.

First, the change pattern of frequency of the AC voltage given to the transducer is only required to be a pattern in which the number of wave of the ultrasonic standing wave is changed by M/2 (where |M| is an integer of 1 or more).

In that case, in order to set the phase shift pitch of the three-beam structured illumination to an arbitrary value $\Delta\psi$, the distance D from one end of the ultrasonic wave propagation path to the center of the spot S, and the total length L of the ultrasonic wave propagation path are only required to satisfy a relation of $D:L=\Delta\psi/M:2\pi$.

Note that a passing area of exit light flux (spot) on the ultrasonic wave propagation path R of the ultrasonic wave spatial light modulator 3 does not always have to be limited to a partial area separated from both ends of the ultrasonic wave propagation path R, for forming the interference fringes on the specimen plane, and when, for example, the light flux passed through the ultrasonic wave propagation path R is narrowed by the field stop 5B, the passing area of effective exit light flux on the ultrasonic wave propagation path R, namely, the partial area on the ultrasonic wave propagation path R through which the exit light flux that contributes to the interference fringes (structured illumination S') formed on the illuminated area (observational area, field area) on the specimen plane passes, is only required to satisfy the relation of $D:L=\Delta\psi/M:2\pi$.

Incidentally, if it is set that M=1, the number of ultrasonic standing wave is changed only by 1/2, so that the deviation occurred, due to the change, in the number of fringe of the three-beam structured illumination can be minimized.

Further, when the number of image data used for the separating calculation is k, if it is set that $\Delta\psi=2\pi/k$, it is possible to securely obtain the required image data. Note that it is preferable that |k| is an integer of 5 or more.

Further, in the three-dimensional mode of the present system, the adjustment of phase difference $\Delta\Psi$ is automatically conducted by the controlling device 19, but, the adjustment may also be conducted manually by a user of the system. However, in that case, it is required that the controlling device 19 displays, in real time, an image output by the imaging device 12, to the image displaying device 14, so that the user can check the contrast of image which is under adjustment.

Further, in the three-dimensional mode of the present system, the duty ratio (ON period/pulse period) of the pulse signal is set to 1/2, but, there is no problem if the duty ratio is set to another ratio. Even when the duty ratio is set to another ratio, the condition of the phase difference $\Delta\Psi$ for increasing the contrast of image of the three-beam structured illumination is the same condition as that of a case where the duty ratio is set to 1/2. However, it is desirable to set the duty ratio to 1/2, in order to increase a utilization efficiency of light.

Further, in the three-dimensional mode of the present system, the frequency of the pulse signal is made to coincide with the frequency of the sine signal, but, there is no problem if the frequency of the pulse signal does not coincide with the frequency of the sine signal as long as the frequency of the pulse signal is 1/N times the frequency of the sine signal (N is an integer of 1 or more).

However, in that case, it is desirable to set the duty ratio (ON period/pulse period) of the pulse signal to 1/(2N). FIG. 13 illustrate an example of case where it is set that N=3, in which FIG. 13(A) illustrates a waveform of time-variation of the refractive index of the antinode a of the ultrasonic standing wave under the setting of N=3, and FIG. 13(B) illustrates a waveform of time-variation of the intensity of incident light.

In this case, although the incident light is incident only once every three pitches (3T) of the refractive index variation, the length of the period of time during which the incident light is incident corresponds to a length of half pitch (T/2) of the refractive index variation, so that by adjusting the aforementioned phase difference $\Delta\Psi$ to an appropriate value, and making the period of time during which the incident light is incident coincide with only either the anterior half period or the last half period of the refractive index variation, the contrast of image can be increased.

Note that although the duty ratio (ON period/pulse period) of the pulse signal is set to coincide with 1/(2N), the duty ratio does not always have to perfectly coincide with 1/(2N), and it is only required to be 1/(2N) or less.

Incidentally, when the duty ratio is set to less than 1/(2N), the length of period of time during which the incident light is incident becomes shorter than the length of half pitch (T/2) of the refractive index variation, but, by adjusting the aforementioned phase difference $\Delta\Psi$ to an appropriate value and making a timing at which the incident light is incident coincide with a timing at which the refractive index indicates a peak or a valley, it is possible to maximize the contrast of image. Note that if the duty ratio is set to less than 1/(2N), and such a timing adjustment is conducted, it can be expected to obtain a clearer image.

Further, in the three-dimensional mode of the present system, the waveform of time-modulation of the intensity of incident light with respect to the ultrasonic wave spatial light modulator is set to the pulse waveform, and on/off of the intensity is realized (incident light is turned on/off), but, a certain effect can be achieved only by changing the intensity of incident light between a high intensity and a low intensity.

Further, in the three-dimensional mode of the present system, the waveform of time-modulation of the light intensity of incident light with respect to the ultrasonic wave spatial light modulator is set to the pulse waveform, but, it is also possible to employ another waveform such as a sinusoidal waveform, instead of the pulse waveform, as long as the light intensity is time-modulated.

Further, in the three-dimensional mode of the present system, the intensity of light that is exited from the coherent light source 1 and is incident on the ultrasonic wave spatial light modulator 3 is modulated, but, it is also possible to directly modulate an intensity of output of the coherent light source 1 to achieve a similar effect.

Further, in the three-dimensional mode of the present system, the intensity of light directed toward the specimen 10 (illumination light) is modulated for improving the contrast of image, but, it is also possible to modulate an intensity of light exited from the specimen 10 (observational light).

Further, in the three-dimensional mode of the present system, the illumination light or the observational light is modulated for improving the contrast of image, but, it is also possible to control the imaging device 12 to achieve a similar effect.

Specifically, in order to improve the contrast of image in the three-dimensional mode of the present system, it is only required to modulate at least one of the intensity of illumination light and the intensity of observational light, or to control the imaging device 12.

Note that in order to modulate the intensity of light exited from the specimen 10 (observational light), it is only required to dispose, for example, a light intensity modulator, a mechanical shutter or the like at an arbitrary position of the optical system from the objective lens 9 to the imaging device 12 (preferably at a position between the second objective lens 11 and the imaging device 12), and to modulate the light intensity modulator or the like using a modulating signal having a frequency which is 1/N times a frequency of a driving signal given to the ultrasonic wave spatial light modulator 3, in a similar manner to that of the modulation of illumination light described above.

Further, in order to achieve the similar effect by controlling the imaging device 12, it is only required to mount an electronic shutter in the imaging device 12, and to modulate the electronic shutter using a modulating signal having a frequency which is 1/N times a frequency of a driving signal given to the ultrasonic wave spatial light modulator 3, for example.

Specifically, an electric charge generated from light received at a light-receiving surface of the imaging device 12 is stored, transferred and photoelectric-converted for every period of time corresponding to a frequency being 1/N times the frequency of the driving signal given to the ultrasonic wave spatial light modulator 3, to thereby generate an electrical signal.

Further, it is set that by modulating the electronic shutter using the modulating signal having the frequency which is 1/N times the frequency of the driving signal given to the ultrasonic wave spatial light modulator 3, the electrical signals obtained as described above are divided into an electrical signal used for an image formation, namely, an electrical signal obtained at a timing which is approximately equal to a frequency that is 1/(2N) times the frequency of the driving signal, and an electrical signal which is obtained at a timing other than the above timing and is not used for the image formation.

Here, the electronic shutter indicates one having a function of dividing the electrical signals obtained for every predetermined period of time into the electrical signal used for the image formation and the electrical signal which is not used for the image formation.

[Supplement Common to Two-Dimensional Mode and Three-Dimensional Mode]

Further, in the above explanation, the position of spot in the ultrasonic wave spatial light modulator 3 is made to be different between the two-dimensional mode and the three-dimensional mode, and in this case, there is generated a necessity of moving the position of the ultrasonic wave spatial light modulator 3 before and after the switching of mode.

Accordingly, in the present system, it is preferable to previously set a switching pattern of the sine signal described above to enable the number of wave of the ultrasonic standing wave to be changed by 1/2, and to previously adjust the positional relationship between the spot S and the ultrasonic wave spatial light modulator 3 so that the distance D from one end of the ultrasonic wave propagation path to the center of the spot S satisfies D:L=1:6.

In this case, in the two-dimensional mode, by changing the number of wave of the ultrasonic standing wave by 1/2, it is possible to set the phase shift pitch of the two-beam structured illumination to "$2\pi/3$".

Further, in this case, in the three-dimensional mode, by changing the number of wave of the ultrasonic standing wave by 1, it is possible to set the phase shift pitch of the three-beam structured illumination to "$\pi/3$".

FIG. 14 illustrates a relation between the number of wave of the ultrasonic standing wave and the amount of phase shift when it is set that D:L=1:6.

Therefore, it is only required that the image storing-calculating device 13 in the two-dimensional mode uses three pieces of image data obtained in each of three states indicated by reference letters a, c, and e in FIG. 14 for the above-described separating calculation.

Meanwhile, the image storing-calculating device 13 in the three-dimensional mode is only required to use six pieces of image data obtained in each of six states indicated by reference letters a to f in FIG. 14 for the above-described separating calculation.

Specifically, in the present system, only by previously adjusting the positional relationship between the spot S and the ultrasonic wave spatial light modulator 3 to the relationship suitable for both of the two-dimensional mode and the three-dimensional mode, it is possible to omit the movement of the ultrasonic wave spatial light modulator 3 before and after the switching of mode.

Figure 4:
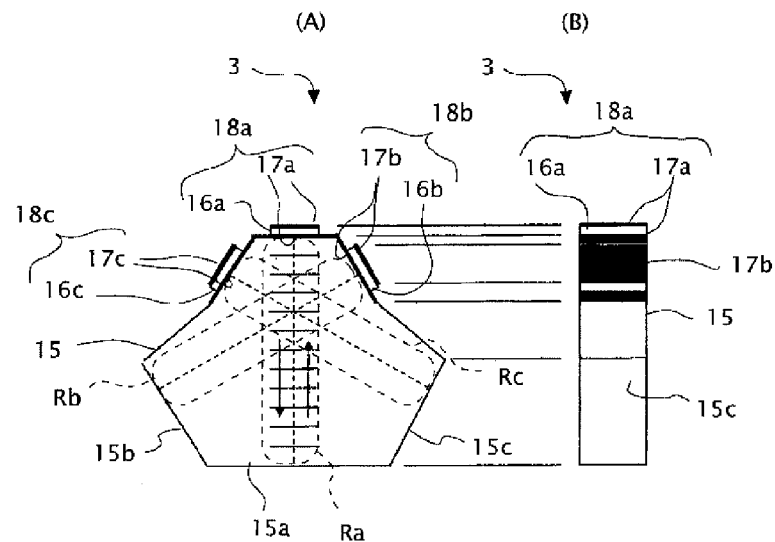
FIG. 4 is a configuration diagram of the ultrasonic wave spatial light modulator 3.

Further, in the acousto-optical medium 15 of the present system, the three ultrasonic wave propagation paths Ra, Rb, and Rc are disposed in an asymmetric relation relative to the center of the spot S (refer to FIG. 4), but, they may also be disposed in a symmetric relation as illustrated in FIG. 15, for example. Incidentally, an advantage of the example illustrated in FIG. 4 is that projections and depressions of the outer shape of the acousto-optical medium 15 are small, and an advantage of the example illustrated in FIG. 15 is that environments of the three ultrasonic wave propagation paths Ra, Rb, and Rc completely coincide with one another.

Further, in the present system, the lengths of the ultrasonic wave propagation paths Ra, Rb, and Rc are set to common, and change patterns of frequency of the AC voltage given to the transducers 18a, 18b, and 18c are set to common, but, it is also possible to set that the respective lengths and change patterns are not common. However, also in that case, the respective ultrasonic wave propagation paths Ra, Rb, and Rc are set to satisfy the above-described conditions.

Further, in the explanation of the present embodiment, it is explained that the number of wave of the ultrasonic standing wave (namely, the wavelength of the ultrasonic standing wave) generated in the ultrasonic wave propagation paths Ra, Rb, and Rc, is changed in the predetermined pattern for shifting the phase of the interference fringes formed of the diffracted lights, and the frequency of AC voltage given to the transducers 18a, 18b, and 18c of the ultrasonic wave spatial light modulator 3 is changed, as one method of changing the wavelength of the ultrasonic standing wave, but, it goes without saying that the present invention is not limited to this method.

Further, in the above-described respective embodiments, as the diffracted lights for forming the interference fringes (two-beam interference fringes, three-beam interference fringes), a combination of ±first-order diffracted lights and 0th-order diffracted light is employed, but, another combination may also be employed. In order to form the three-beam interference fringes, it is only required to generate three-beam interference caused by three diffracted lights in which an interval of orders of diffraction is equal, so that a combination of 0th-order diffracted light, first-order diffracted light, and second-order diffracted light, a combination of ±second-order diffracted lights and 0th-order diffracted light, a combination of ±third-order diffracted lights and 0th-order diffracted light, and the like can be employed.

Note that all documents disclosed in the present specification are incorporated by reference.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be restored to, falling within the scope thereof.

What is claimed is:

1. A structured illuminating microscopy, comprising:
    a light modulator disposed in a light path of an exit light flux from a light source, and in which a sonic wave propagation path is arranged in a direction traversing the exit light flux;
    a generator generating a sonic standing wave in the sonic wave propagation path by giving a driving signal for vibrating a medium of the sonic wave propagation path to the light modulator;
    an illuminating optical system making at least three diffracted components of the exit light flux passed through the sonic wave propagation path to be interfered with one another, and forming interference fringes of the diffracted components on an observational object;
    an image-forming optical system forming an image by an observational light flux from the observational object on a detector; and
    a controller controlling a contrast of an image obtained from the detector by modulating at least one of (i) an intensity of the exit light flux, (ii) an intensity of the observational light flux, and (iii) detecting time of the detector with a modulating signal having a frequency which is 1/N times a frequency of the driving signal, where N is an integer of 1 or more.

2. The structured illuminating microscopy according to claim 1, wherein
    the controller sets a duty ratio of the modulating signal to 1/(2N) or less.

3. The structured illuminating microscopy according to claim 1, wherein
    the controller modulates the intensity of the exit light flux by giving the modulating signal to at least one of the light source and an intensity modulator disposed in the light path of the exit light flux.

4. The structured illuminating microscopy according to claim 1, wherein
    the controller modulates the intensity of the observational light flux by giving the modulating signal to an intensity modulator disposed in a light path of the observational light flux.

5. The structured illuminating microscopy according to claim 3, wherein
    the intensity modulator is disposed between the light source and the light modulator.

6. The structured illuminating microscopy according to claim 1, wherein:
    the interference fringes are formed of the exit light flux passed through a predetermined partial area separated from both ends of the sonic wave propagation path; and
    the generator shifts a phase of the interference fringes by changing a wavelength of the sonic standing wave in a predetermined pattern.

7. The structured illuminating microscopy according to claim 6, wherein:
    the generator is capable of changing the wavelength of the sonic standing wave in a pattern in which a total number of wave of the sonic standing wave is changed by M/2, where |M| is an integer of 1 or more; and
    when a phase shift pitch of the interference fringes is set to $\Delta\psi$, a distance D from either end portion of the sonic wave propagation path to the partial area and a total length L of the sonic wave propagation path satisfy a relation of $D:L=\Delta\psi/M:2\pi$.

8. The structured illuminating microscopy according to claim 6, wherein
    the generator changes the wavelength of the sonic standing wave by changing the frequency of the driving signal given to the light modulator in a predetermined pattern.

9. The structured illuminating microscopy according to claim 1, further comprising
    a mask switching mechanism switching a mode of the structured illuminating microscopy between a three-dimensional mode in which at least three diffracted components of the exit light flux are reflected on the interference fringes, and a two-dimensional mode in which only two diffracted components of the exit light flux are reflected on the interference fringes.

10. The structured illuminating microscopy according to claim 9, wherein:
    the interference fringes are formed of the exit light flux passed through a predetermined partial area separated from both ends of the sonic wave propagation path;
    the generator shifts a phase of the interference fringes by changing a wavelength of the sonic standing wave in a predetermined pattern; and
    a distance D from either end portion of the sonic wave propagation path to the partial area and a total length L of the sonic wave propagation path satisfy a relation of $D:L=1:6$.

11. The structured illuminating microscopy according to claim 1, wherein
    the light modulator has a plurality of the sonic wave propagation paths which intersect at a passing area of the exit light flux, and a direction of the sonic standing wave is capable of being switched by switching an effective sonic wave propagation path among the sonic wave propagation paths.

12. The structured illuminating microscopy according to claim 1, further comprising
    a calculator calculating a super-resolved image of the observational object based on a plurality of images obtained by the detector under each of a plurality of states in which patterns of the sonic standing wave are different.

13. A structured illuminating observation method, comprising:
    preparing a light modulator disposed in a light path of an exit light flux from a light source, and in which a sonic wave propagation path is arranged in a direction traversing the exit light flux;

generating a sonic standing wave in the sonic wave propagation path by giving a driving signal for vibrating a medium of the sonic wave propagation path to the light modulator;

making at least three diffracted components of the exit light flux passed through the sonic wave propagation path to be interfered with one another, and forming interference fringes of the diffracted components on an observational object;

forming an image by an observational light flux from the observational object on a detector; and controlling a contrast of an image obtained from the detector by modulating at least one of (i) an intensity of the exit light flux, (ii) an intensity of the observational light flux, and (iii) detecting time of the detector with a modulating signal having a frequency which is 1/N times a frequency of the driving signal, where N is an integer of 1 or more.

* * * * *